United States Patent [19]

Takagi et al.

[11] 4,066,507

[45] Jan. 3, 1978

[54] PROCESS FOR PRODUCING L-LEUPEPTINS

[75] Inventors: Kenkichi Takagi, Ageo; Yukio Yamamoto, Tokyo; Tadao Yamazaki, Yono; Hiroshi Yamaguchi, Urawa; Hamao Umezawa, Tokyo, all of Japan

[73] Assignee: Nippon Kayaku Kabushiki Kaisha, Tokyo, Japan

[21] Appl. No.: 731,894

[22] Filed: Oct. 13, 1976

[51] Int. Cl.$^2$ .............................................. C12D 13/06
[52] U.S. Cl. .................................................... 195/80 R
[58] Field of Search ................................. 195/80 R, 65

[56] References Cited

U.S. PATENT DOCUMENTS 3,840,513  10/1974  Umezawa et al. ................. 260/112.5

*Primary Examiner*—Lionel M. Shapiro
*Attorney, Agent, or Firm*—Schuyler, Birch, Swindler, McKie & Beckett

[57] ABSTRACT

DL-leupeptins have been known to be produced by leupeptins-producing organisms and only L-leupeptins have bioactivity. This invention provides the processes for production of L-leupeptins in high yield and for its extraction without racemization.

L-leupeptins may be efficiently produced by inoculating a leupeptins-producing strain of Streptomyces into a medium containing nutrient sources and aerobically cultivating under the condition of pH 5.0 to 7.0. Production of L-leupeptins is markedly increased by adding to the medium each 0.5 to 1.25% (wt/vol) of L-leucine, L-arginine (as hydrochloride), and glycine, and is further increased by adding to the medium 0.05 to 0.3% (wt/vol) of at least one of the yeast extract, casein hydrolyzate, and ribonucleic acids, in addition to the above amino acids. Efficient separation of L-leupeptins of acceptable purity from the cultured broth can be effected by use of a nonionic adsorbent resin, wherein the pH is controlled always to be 7.0 or lower. L-leupeptins thus obtained inhibit plasmin, tripsin, cathepsin B and papain, and the ointment containing L-leupeptins have been confirmed to be effective in treatment of inflammation, ulceration and burn of skin surface, erythematosis, skin transplantation, etc.

7 Claims, 2 Drawing Figures

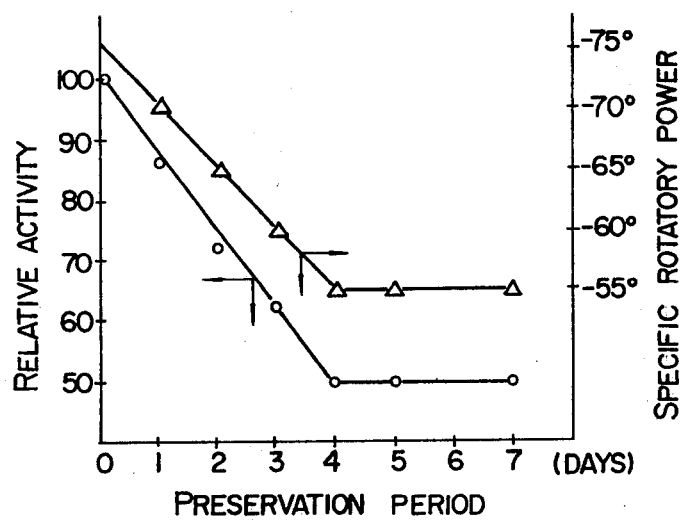

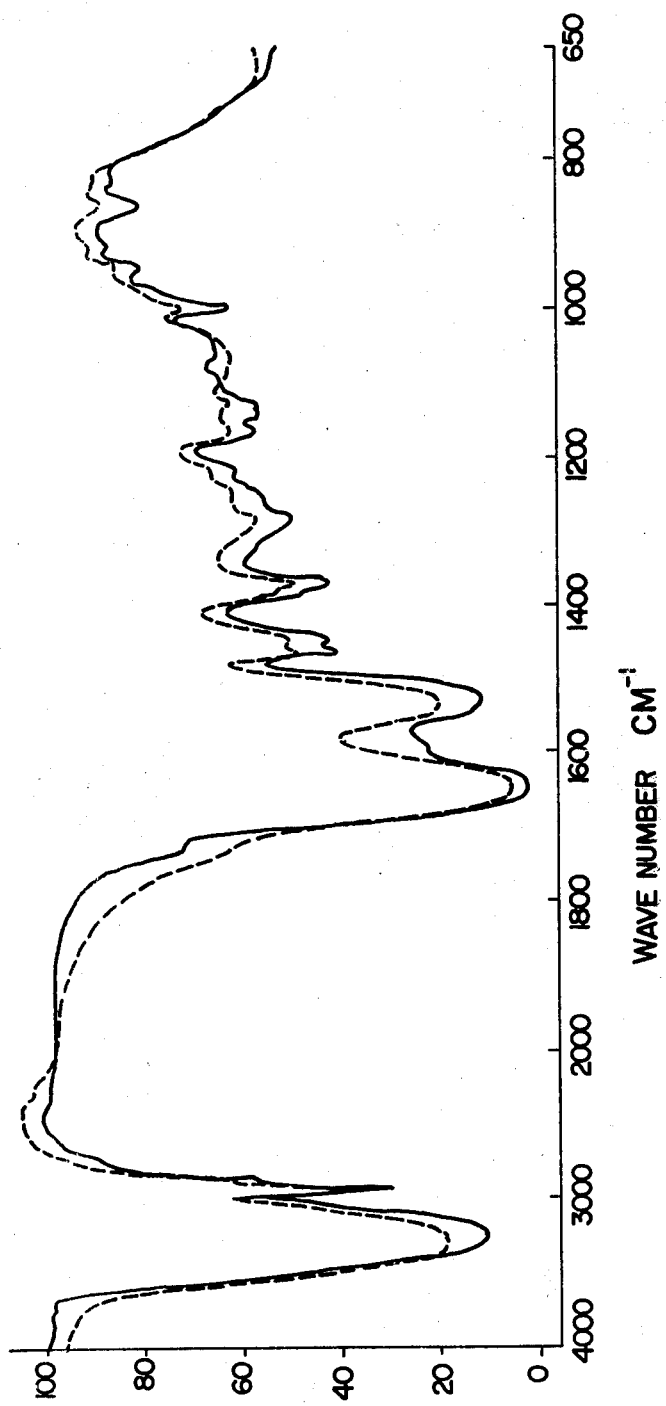

PROCESS FOR PRODUCING L-LEUPEPTINS

This invention relates to a processes for producing L-leupeptins by fermentation and their extraction and purification from fermented beer.

Leupeptins are enzyme inhibitors which were found by Umezawa, one of the present inventors and his collaborators in culture filtrates of *Streptomyces roseus* and a great varity of microorganisms of Streptomyces. The chemical structures of leupeptins are represented by the following general formula:

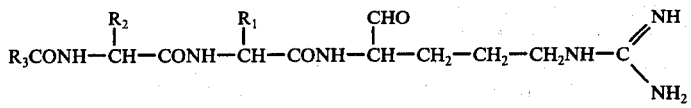

wherein $R_1$ and $R_2$ are each $-CH_2-\underset{\underset{CH_3}{|}}{CH}-CH_3$, $-\underset{\underset{CH_3}{|}}{CH}-CH_2-CH_3$, or $-\underset{\underset{CH_3}{|}}{CH}-CH_3$ and $R_3$ is $-CH_3$ or $-C_2H_5$.

These leupeptins are useful substances, being of low toxicity and having protease inhibiting activities such as anti-plasmin and anti-trypsin activities, and having anti-inflammatory and various other pharmacological effects (cf. Japanese Pat. No. 595,140, U.S. Pat. No. 3,840,513).

Main components of leupeptins hitherto obtained by fermentation are propionyl- and acetyl-L-leucyl-L-leucyl-DL-argininal having each an argininal group of the DL-steric configuration (hereinafter referred to as DL-leupeptins or DL-form) [Kondo, S. et al., Chem. Pharm. Bull. (Tokyo), 17, 1896 (1969); U.S. Pat. No. 3,840,513]. Until this invention, L-leupeptins have never been obtained by fermentation and therefore it has been considered that DL-leupeptins are produced by fermentation.

Shimizu et al. chemically synthesized leupeptins having an argininal group of L-configuration (herein-after referred to as L-leupeptins or L-form) and other leupeptins having an argininal group of D-configuration (hereinafter referred to as D-leupeptins or D-form). On biochemical test, they confirmed that the active principle responsible for the inhibitory effects on enzymes is L-leupeptins, while D-leupeptins are inactive and that DL-leupeptins obtained by fermentation exhibit only one-half the activity of L-leupeptins [Shimizu, B. et al., J. Antibiotics, 25, 515 (1972); Umezawa, H., Enzyme Inhibitors of Microbial Origin, University of Tokyo Press (1972), p. 24 - 25].

The present inventors conducted extensive studies on the fermentation procedure and on the extraction and purification procedures, and as the result, they first found the facts itemized below and those findings have led to the present invention.

An object of the present invention is to provide novel processes for producing L-leupeptins by fermentation.

Other object of the present invention is to provide novel processes for extracting and purifying L-leupeptins formed in a culture broth by fermentation.

Further objects and advantages of the present invention will be apparent from the following descriptions.

FIG. 1 of the accompanied drawings represents the progress of racemization of the L-leupeptin obtained by the present process, in terms of relative activity and specific rotatory power both measured as function of the preservation period in days.

In FIG. 2 are shown infrared absorption spectra of the L-leupeptin hydrochloride (shown in solid line) obtained by the present process and DL-leupeptin hydrochloride prepared by conventional fermentation and extraction method (shown in broken line).

1. In the leupeptin fermentation, where pH of cultivation medium is maintained within the range of 5.0 to 7.0, L-leupeptins are accumulated in the medium, whereas in the case when the reaction of medium is shifted to the alkaline side, there are obtained DL-leupeptins. Even when pH of cultivation medium is maintained within the range of 5.0 to 7.0, continued cultivation after the accumulation of L-leupeptins has reached the maximum causes partial racemization of the accumulated L-leupeptins and give L-leupeptins contaminated with D-form.

2. Purified L-leupeptins also undergo gradual racemization in a faintly alkaline medium, e.g., pH 8.0, under a mild temperature condition, e.g. 23° C, and transform completely into DL-form after several days.

3. In typical known methods of purification, leupeptins in the culture filtrate are subjected to adsorption and desorption treatments by using a column of activated charcoal or an ion exchange resin of the carboxylic acid type such as Lewatit CNP (trademark for a cation-exchange resin containing carboxylic acid group, manufactured by Bayer Co.) or Amberlite IRC-50 (trademark for a cation-exchange resin containing carboxylic acid group, manufactured by Rohm and Haas Co.) in H—, Na— or mixed form. In the case of cation exchange resins of the carboxylic acid type, the H-form does not induce racemization of L-leupeptins but is not economical because of its low adsorptive capacity, while the Na-form has a still lower adsorptive capacity and, moreover, causes complete racemization. Although a mixed type of H— and Na-forms in a proper ratio (7–8: 3–2 by volume) is superior to any other known adsorbent because of its highest adsorptive capacity and high yields in adsorption and desorption, it is unsuitable for obtaining L-leupeptins, because it causes strong racemization even if the treatments were carried out in weakly or moderately acidic condition.

4. The method involving adsorption of leupeptins from a culture filtrate on an activated charcoal and succeeding desorption with an acidic aqueous organic solvent, e.g. 80% methanol of pH 2.0, afforded DL-leupeptins when it was applied to the beer fermented by conventional methods without pH control. The present inventors found that this method gives L-leupeptins when applied to the beer prepared by methods developed in this invention. However, the yield was low as 30 to 50%. It is to be noted, however, that activated charcoal is useful, similarly to silica gel or alumina, as an adsorbent for use in column chromatography in the succeeding purification step.

5. The method of this invention which utilizes a porous nonionic adsorbent resin is applicable to both the first extraction-purification step involving adsorption of leupeptins from a culture filtrate and desorption of the adsorbed leupeptins and the later step of further purifying L-leupeptins in the prepurified L-leupeptins-containing solution, said application to the first step being especially advantageous. When a culture filtrate containing leupeptins is treated according to the present method, there are manifested far greater advantages over any other known method, such as a far greater adsorptive capacity as compared with any conventional method, absence of racemization of L-leupeptins, and a high yield of about 90% in the adsorption-desorption step.

6. By the addition of each 0.5 to 1.25% of L-leucine, L-arginine (as hydrochloride), and glycine to the L-leupeptins fermentation medium, production of L-leupeptins is increased to 4 – 6 times that obtained by conventional methods.

7. The yield of L-leupeptins is further increased to as high as 7 – 10 times that obtained by conventional methods by further adding to the above medium containing the said amino acids at least one of the various natural organic substances such as ribonucleic acids, yeast extract, and casein hydrolyzate.

8. When a fermentation medium containing the above-noted three amino acids, which medium does not contain more than 0.3% (wt/vol) of amino acids including amino acids themselves and substances containing them such as peptides, proteins, etc. other than above-noted three amino acids, is used, the leupeptin product consists substantially of acetyl-L-leucyl-L-leucyl-L-argininal alone and contains no other leupeptins containing propionyl group, isoleucine residue, or valine residue.

By the accomplishment of this invention on the basis of the aforesaid findings, there have been first established processes for producing L-leupeptins, which are an active form, in high yield by fermentation. It is also an important finding for the production of only one leupeptin of the constant quality that L-leupeptin consisting of acetyl-L-leucyl-L-leucyl-L-argininal alone may be obtained in high yield by carrying out the present process using a culture medium which contains each 0.5 to 1.25% of L-leucine, L-arginine (as hydrochloride), and glycine and does not contain more than 0.3% (wt/vol) of amino acids including amino acids themselves and substances containing them such as peptides, proteins, etc. other than above-noted three amino acids.

The advantages of the present invention are illustrated below with reference to Experimental Examples.

In the present invention, the potency of leupeptins was measured in the following way.

0.5 Milliliter of a leupeptin solution prepared so that the concentration may become about 8 mcg (potency)/ml was added to 2.5 ml of a $1.25 \times 10^{-4}$ M solution of p-toluenesulfonyl-L-arginine methyl ester hydrochloride in Tris-buffer of pH 8.1. After pre-incubation at 32° C for 5 minutes, to the mixture was added 0.1 ml of an aqueous trypsin solution (7.5 mcg/ml). Immediately after having been incubated at 32° C for 30 minutes, the reaction mixture was tested for absorbance at 247 nm to obtain the test value. The blank value was obtained in the same manner as mentioned above, except that leupeptin was not added. Degree of trypsin inhibition was calculated by dividing the difference between the blank value and the test value by blank value. According to this test method, the 50% trypsin inhibition concentration ($ID_{50}$) of acetyl-L-leucyl-L-leucyl-L-argininal hydrochloride of the highest purity was 0.98 mcg/ml. This substance was used as standard sample and the potency of leupeptins was expressed in weight, such as mcg (potency) and mg (potency).

DL-leupeptins of the highest purity obtained by the conventional fermentation and purification methods showed an $ID_{50}$ of 1.87 mcg/ml.

The L-leupeptins content of a mixture of L-leupeptins and D-leupeptins was measured in the following way.

The leupeptins under test were brought into an aqueous solution and oxidized with potassium permanganate to leupeptin acids (the argininal portion of leupeptin had been oxidized to form arginine). The resulting acids were purified and isolated by activated charcoal chromatography and acidic alumina chromatography. The isolated acids were hydrolyzed with 6N hydrochloric acid at 110° C for 24 hours. The total arginine content of the hydrolyzate was determined by means of an amino acid analyzing instrument. On the other hand, the L-arginine content of the hydrolyzate was determined by bioassay using lactic-acid bacteria. The L-arginine content (%) of the total arginine was assumed to be equal to the L-leupeptins content (L-form percentage) in the total leupeptins. The L-form content of the standard sample was 100% and that of the DL-leupeptins obtained by conventional fermentation methods was 52%.

EXPERIMENTAL EXAMPLE 1

A slant culture of Streptomyces roseus MA839-A1 (FERM-P No. 3017; ATCC 31245) was inoculated into 100 ml of a medium containing 2% of glucose, 2% of starch, 3% of polypeptone, 0.5% of NaCl, and 0.3% of $KH_2PO_4$, which had been placed in a flask and sterilized, and then subjected to shake-culture at 27° to 28° C for 2 days to prepare the inoculum (the percentage used herein is the weight per volume percentage and the same applies hereinafter). Twenty liters of the same medium as mentioned above was prepared in a 30 liter jar fermentor and inoculated with 200 ml of the above inoculum. Cultivation was carried out at 27° C with aeration and agitation. At regular intervals, a portion of the culture broth was withdrawn and purified, without racemization, according to the present invention, to obtain purified leupeptin hydrochlorides in powder form. The results of test for the activity and L-form percentage were as shown in Table 1.

Table 1

| Cultivation period (hour) | Change with time in leupeptin fermentation | | | | | |
|---|---|---|---|---|---|---|
| | 24 | 36 | 42 | 48 | 60 | 72 |
| pH | 6.6 | 6.9 | 6.5 | 5.5 | 4.9 | 5.6 |
| Potency of cultured broth (mcg/ml) | 20 | 115 | 330 | 450 | 320 | 280 |
| Potency of leupeptin powder (mcg/mg) | — | — | 1000 | 1000 | 910 | 820 |
| L-form % of leupeptin powder | — | — | 100 | 100 | 92 | 84 |

As is apparent from Table 1, the potency of leupeptin powder was 1,000 mcg/mg after 42 hours and 48 hours of cultivation, whereas it decreased to 910 mcg/mg after 60 hours and further to 620 mcg/mg after 72 hours of cultivation. The L-form content of the leupeptin powder was also decreased from 100% after 42 hours and 48 hours of cultivation to 92% after 60 hours and further to 84% after 72 hours of cultivation. Therefore, care must be taken so as to avoid unnecessarily prolonged cultivation, because even when pH was controlled within the range of 5.0 to 7.0, prolonged cultivation after maximum accumulation of L-leupeptins has been attained seems to cause partial racemization of the L-leupeptins already produced.

EXPERIMENTAL EXAMPLE 2

The L-leupeptin hydrochlorides obtained after 48 hours of cultivation in Experimental Example 1 were dissolved in 0.1 M phosphate buffer of pH 8.0 to make 1% solution. The resulting was left standing at 23° C and the changes with time in specific rotatory power and in relative activity (mcg/mg) were measured. The results obtained were as shown in FIG. 1. The leupeptins recovered after 7 days showed an L-form content of 50% and a relative activity of 490 mcg/mg, indicating that complete racemization had occurred. It is evident from the above results that L-leupeptins undergo racemization even under such mild conditions as pH of 8.0 and a temperature of 23° C.

EXPERIMENTAL EXAMPLE 3

By using the culture broth obtained after 48 hours of cultivation conducted in the same manner as in Experimental Example 1, the following two purification methods were compared with each other.

Method A: The culture broth of pH 6.0 was passed through a column of Lewatit ® CNP-80 (Na— form : H-form = 2 : 8 by volume) to adsorb L-leupeptins. The adsorbate was eluted with 80% methanol containing 1 N hydrochloric acid. All eluate fractions were acidic. The active fractions were evaporated to result an aqueous solution. From the aqueous solution, leupeptins were extracted with n-butanol and the n-butanol solution was evaporated under reduced pressure to remove n-butanol. The resulting aqueous solution was passed through an activated charcoal column and the adsorbed phase was developed with 20% aqueous acetone which had been adjusted to pH 2.0 with hydrochloric acid. The active effluent fractions were collected and neutralized with Dowex 44 (OH-form) (a polyamine resin composed of primary, secondary, and tertiary amines, manufactured by Dow Chemical Co.), then concentrated, and freeze-dried. The powder obtained was dissolved in methanol and adsorbed on an acidic alumina column filled with methanol, and then developed with methanol. The active effluent fractions were collected and evaporated to dryness to obtain purified L-leupeptin hydrochlorides. The yield from culture filtrate was 33%.

Method B: The same culture filtrate as in the method A was passed through a column of Amberlite XAD-2 (trademark of a nonionic adsorbent resin consisting of a copolymer of styrene and divinylbenzene, manufactured by Rohm and HAAS Co.) to adsorb leupeptin and the adsorbed phase was then eluted with 50% methanol of pH 2.0. The active eluate fractions were collected and freed from methanol by distillation, leaving behind an aqueous solution. Leupeptins were extracted with n-butanol from the aqueous solution and the following processes of n-butanol extraction were treated in the same manner as in the method A to obtain purified leupeptin hydrochlorides. The yield from the culture filtrate was 65%. The results obtained by the two methods were compared as shown in Table 2.

Table 2

| | Comparison between methods A and B | | |
|---|---|---|---|
| Method | Yield, % | Potency of powder, mcg/mg | L-form content of powder, % |
| A | 33 | 530 | 56 |
| B | 65 | 1,000 | 100 |

From the above results it is apparent that in extracting and purifying L-leupeptins, if adsorption-desorption was effected by using a weakly acidic ion-exchange resin of the carboxylic acid type partially converted into Na-form, a considerable proportion of L-leupeptin undergoes racemization, even when the solutions containing leupeptins remain acidic.

EXPERIMENTAL EXAMPLE 4

Comparison of leupeptin productivity between the medium of this invention and the conventional medium 1. Medium condition
  1. Medium of this invention: 3% glycerol, 0.75% L-leucin, 0.75% L-arginine hydrochloride, 0.75% glycine, 0.5% $NH_4NO_3$, 0.5% NaCl, 0.3% $K_2HPO_4$
  2. Conventional medium for production (control): 1% glucose, 2% starch, 3% peptone, 0.5% NaCl, 0.3% $KH_2PO_4$ (cf., Japanese Patent No. 595,140; U.S. Pat. No. 3,840,513)
  3. Conventional synthetic medium (control): 1% glucose, 1% starch, 0.26% L-leucin, 0.4% arginine hydrochloride, 0.3% glycine, 0.2% $NH_4NO_3$, 0.1% $K_2HPO_4$, 0.05% $MgSO_4$. $7H_2O$, 0.05% KCl, 0.001% $FeSO_4.7H_2O$ [cf., Umezawa, H., Enzyme Inhibitors of Microbial Origine, University of Tokyo Press (1972), p. 20]

2. Strain used: The same as used in Experimental Example 1.

3. Cultivation condition: One hundred milliliters of the medium placed in a 500 ml flask was inoculated with 1 ml of the inoculum cultured in the same manner as in Experimental Example 1. The inoculated medium was cultured at 27° to 28° C on a shaking machine operating at an amplitude of 7 cm and 135 reciprocations per minute. Samples were withdrawn after 48 and 72 hours and tested for the potency of leupeptins.

4. Results: The results obtained were as shown in Table 3.

Table 3

| | Period of culture | |
|---|---|---|
| Medium | 48 hours | 72 hours |
| Medium of this invention | 1,650 mcg/ml | 2,500 mcg/ml |
| Conventional medium for production | 520 " | 630 " |
| Conventional synthetic medium | 380 " | 440 " |

As is apparent from Table 3, in 72 hours of cultivation, the leupeptin productivity of the medium of this invention reached 4 to 6 times those of the conventional medium for production and conventional synthetic medium used as controls. In spite of comprising almost the same ingradients, the yield obtained with the medium of this invention was as high as 6 times that obtained with the conventional synthetic medium, because in the medium of this invention the concentrations of L-leucine, L-arginine, and glycine and the balance among them had been improved.

EXPERIMENTAL EXAMPLE 5

Suitable range of the amounts of L-leucine, L-arginine, and glycine

1. Medium condition: Varied amounts of L-leucine, L-arginine hydrochloride, and glycine, as shown in Table 4, were added to the basal medium comprising 3.0% glucose, 0.5% $NH_4NO_3$, 0.1% $K_2HPO_4$, 0.5% $MgSO_4.7H_2O$, 0.05% KCl, 0.2% ribonucleic acid, and 0.1% silicone defoamer oil.

2. Strain used: the same as used in Experimental Example 1.

3. Cultivation condition: the same as in Experimental Example 4.

4. Results: the results obtained were as shown in Table 4.

Table 4

| Amounts added, % | | | Yield of leupeptin, mcg/ml | |
|---|---|---|---|---|
| L-leucine | L-ariginine hydrochloride | Glycine | 48 hours | 72 hours |
| 0.25 | 0.25 | 0.25 | 310 | Insignificant |
| 0.50 | 0.50 | 0.50 | 2,080 | 3,300 |
| 0.75 | 0.75 | 0.75 | 3,460 | 4,370 |
| 1.00 | 1.00 | 1.00 | 2,080 | 2,860 |
| 1.25 | 1.25 | 1.25 | 400 | 2,560 |
| 1.50 | 1.50 | 1.50 | Insignificant | Insignificant |

As seen from Table 4, when L-leucine, L-arginine hydrochloride, and glycine were added to the medium in an amount of each 0.25%, the yield of leupeptin in 72 hours of cultivation was insignificant, whereas when each 0.5 to 1.25% of said amino acids were added, the yield of leupeptin in the same period of cultivation was as high as 2,560 to 4,370 mcg/ml. However, when the amount of said amino acids was increased to each 1.50%, only insignificant amount of leupeptin was produced. These results confirmed that a high yield of leupeptin is obtained specifically when each 0.5 to 1.25% of L-leucine, L-arginine (as hydrochloride), and glycine is added to the medium.

EXPERIMENTAL EXAMPLE 6

Effect of addition of natural complex organic substances

1. Medium condition: Natural organic substances shown in Table 5 were added to the medium of this invention used in Experimental Example 4.

2. Strain used: The same as used in Experimental Example 1.

3. Cultivation condition: The same as in Experimental Example 4.

4. Results: The results obtained were as shown in Table 5.

Table 5

| Additives | Amount added, % | Yield of leupeptin, mcg/ml | |
|---|---|---|---|
| | | Cultivation period | |
| | | 48 hours | 72 hours |
| Yeast extract | 0.1 | 1,550 | 2,250 |
| " | 0.2 | 1,770 | 2,300 |

Table 5-continued

| Additives | Amount added, % | Yield of leupeptin, mcg/ml | |
|---|---|---|---|
| | | Cultivation period | |
| | | 48 hours | 72 hours |
| Casamino acids | 0.1 | 1,970 | 2,540 |
| " | 0.2 | 1,780 | 2,550 |
| Ribonucleic acids | 0.1 | 2,040 | 3,420 |
| " | 0.2 | 2,050 | 3,520 |
| Control | 0 | 1,380 | 1,750 |

As is apparent from Table 5, when 0.1 to 0.2% of yeast extract, casamino acids, or ribonucleic acids had been added to the original medium of this invention (used as control), the yield of leupeptin was further increased; particularly when ribonucleic acids were added, the yield was increased to twice the yield obtained with the original medium.

Any of the microorganisms capable of producing L-leupeptins can be used in the present processes. Examples of such microorganisms are *Streptomyces roseus* [2 strains, their Laboratory Numbers of Institute of Microbial Chemistry were MA839-A1, MB262-M1; MA839-A1 was deposited in Fermentation Research Institute, Agency of Industrial Science and Technology, Japan (Kogyo Gijutsuin Biseibutsu Kogyo Gijutsu Kenkyusho) and American Type Culture Collection, Md., U.S.A., deposit numbers being FERM-P No. 3017 and ATCC 31245, respectively], *Streptomyces roseochromogenes* (3 strains, MA943-M1, MB 456-AE1, MB270-A2), *Streptomyces chartreusis* (1 strain, MB58-MG1), *Streptomyces albireticuli* (1 strain, MB26-A1), *Streptomyces thioluteus* (1 strain, MB321-A1), *Streptomyces lavendulae* (1 strain, MB172-A2), and *Streptomyces noboritoensis* (1 strain, MB46-AG). The properties of these species have been described in "The Actinomycetes," vol. II (by S. A. Waksman, The Williams & Wilkins Company, 1961).

The carbon sources which can be used in the leupeptins-producing medium of this invention are acetic acid, glycerol, glucose, sucrose, maltose, dextrin, starch and others; of these, particularly useful are glycerol and glucose. As the inorganic nitrogen source, ammonia nitrogen in superior to nitrate nitrogen.

The amino acids to be added to the medium are L-leucine, L-arginine, and glycine.

The natural organic substances added to the medium include ribonucleic acids, yeast extract, and casein hydrolysate; ribonucleic acids may be of purified grade or raw grade and substances containing ribonucleic acids in relatively high concentrations may also be used.

The porous nonionic adsorbent resins which are used in this invention are for example, Amberlite XAD-1, XAD-2, XAD-4, XAD-5 (which are trademarks, and manufactured by Rohm and Haas Co., U.S.A.) and Diaion HP10, HP20, HP30, HP40, HP50 (which are trademarks, and manufactured by Mitsubishi Chemical Co., Japan), (these nine resins are composed of styrene-divinylbenzene copolymer), Amberlite XAD-7, XAD-8 (trademarks for adsorbents composed of acrylic ester polymer, manufactured by Rohm and Haas Co.), and Duolite S-30 (trademark for an adsorbent composed of phenolic resin, manufactured by Chemical Process Co., U.S.A.).

L-leupeptins are produced according to the present processes in the following manner.

The culture medium contains, for example, 1.0 – 6.0% glycerol, 0.1 – 1.0% $NH_4NO_3$, 0.05 – 0.5%

$K_2HPO_4$, 0.01 – 0.1% $MgSO_4.7H_2O$, 0.01 – 0.1% KCl, 0.5 – 1.25% L-leucine, 0.5 – 1.25% L-arginine (as hydrochloride), 0.5 – 1.25% glycine, 0.05 – 0.3% natural organic substances such as ribonucleic acid, yeast extract and casein hydrolysate, and 0.01 – 0.3% silicon defoamer (pH 6.5). After having been sterilized in a customary way, the medium is aseptically inoculated with a seed culture prepared by cultivating a leupeptins-producing strain such as *Streptomyces roseus*, strain MA839-A1 1 (FERM-P No. 3017; ATCC31245) and then cultured at 23° to 37° C, preferably 25° to 30° C. In the case when pH exceeded 7.0, pH was adjusted to 6.0 to 6.5 by addition of sulfuric acid or phosphoric acid. Usually after 3 to 4 days fermentation, the accumulation of L-leupeptins will reach maximum.

The culture broth thus obtained is filtered and the filtrate is treated with a resin to recover L-leupeptins. The resin treatment can be carried out in various ways but most efficiently by use of a column of resin. The adsorbent resin is packed in a column, then activated by passing, for example, 80% aqueous methanol through the resin, and thoroughly washed with water. The leupeptins-containing culture filtrate is adjusted to pH 5.0 to 6.0 approximately and passed through the resin column to adsorb leupeptins on the resin. After adsorption, the column is washed with water and the adsorbed leupeptins are eluted. The eluents which can be used are lower alcohols such as methanol, ethanol, n-propanol, isopropanol, n-butanol, and isobutanol; aqueous lower alcohols; aqueous acetone; aqueous methyl ethyl ketone; organic solvents containing acidic water; and acidic water. Examples of desirable eluents are 10 to 95% aqueous methanol adjusted to pH 4.0 or less with an inorganic acid such as hydrochloric acid, sulfuric acid, nitric acid, or phosphoric acid. A suitable space velocity of the liquid is 0.5 to 2.0 in the adsorption stage and 0.1 to 1.0, particularly about 0.5, in the elution stage. The eluate is collected in the fractions of definite quantities. A leupeptins-containing portion of the eluate is obtained by combining those fractions which show antitrypsin activity, positive Sakaguchi reaction, or positive Rydon-Smith reaction. Thus, a partially purified solution of L-leupeptins can be obtained by carrying out the adsorption and desorption under acidic condition. Since no commercially economical method for the separation of D- and L-leupeptins has yet been found, it is necessary for the production of L-leupeptins by fermentation to take measures capable of preventing racemization of L-leupeptins throughout the operational steps of fermentation and purification. One of the major advantages of the present processes is that the process permits of efficient recovery of L-leupeptins from a culture broth filtrate containing only L-leupeptins. Further purification of the L-leupeptins thus obtained can be effected by a suitable combination of known purification techniques such as chromatography under acidic condition with activated charcoal, alumina (preferably acidic alumina), or silica gel and extraction from an aqueous solution with n-butanol or the like.

The invention is illustrated below in detail with reference to Examples, but not limited thereto.

EXAMPLE 1

A medium containing 2% glucose, 2% starch, 3% polypepton, 0.5% NaCl, and 0.3% $KH_2PO_4$ and having pH of 7.0 was divided into 100 ml portions. Each 100 ml portion was placed in a 500 ml shaking-flask and sterilized at 120° C for 20 minutes. The sterilized medium was inoculated with one platinum-loopful of a slant culture of a leupeptins-producing strain [Streptomyces roseus, MA839-A1 (FERM-P No. 3,017; ATCC 31245)] and shake-cultured at 27° C for 2 days. Two hundred milliliters of the resulting culture broth was inoculated into a 30 liter jar-fermentor containing 20 liters of the same medium as used above and cultivated at 27° C for 48 hours at an air-flow rate of 20 liters per minute, and agitation of 400 r.p.m. Samples withdrawn after 24, 36, 42, and 48 hours of cultivation showed pH of 6.7, 6.8, 6.4, and 6.7, respectively, and leupeptin potency of 35, 230, 420, and 670 mcg/ml. respectively.

The culture broth thus obtained was admixed with 5% (wt/vol) of a filter aid (Hyflo Super-Cel, Manufactured by Johns-Manville Co., U.S.A.), then filtered, and adjusted with dilute hydrochloric acid to pH 5.5 to obtain about 15 liters of culture filtrate which showed a leupeptin potency of 665 mcg/ml. Four liters (total potency = 2,660 mg unit) of the culture filtrate was passed through a column packed with 100 ml of Amberlite XAD-2, a nonionic adsorbent resin, at a space velocity of 1 to adsorb leupeptins on the resin. After having been washed with water, the adsorbed leupeptins were eluted with 80% aqueous methanol adjusted to pH 2.0 with hydrochloric acid. The active eluate fractions were combined, then freed from methanol by distillation under reduced pressure, and the residual aqueous solution was adjusted to pH 5.5 with dilute sodium hydroxide solution to obtain 100 ml of an aqueous solution of 24.5 mg potency/ml (the yield from the culture filtrate was 92%). This aqueous solution was extracted twice with 70 ml of n-butanol and the combined extract layer was freed from n-butanol by distillation under reduced pressure while adding water, to give 50 ml of an aqueous solution having a potency of 47 mg/ml (total potency was 2,350 mg unit and the yield from the culture filtrate was 88%). The aqueous solution thus obtained was adjusted to pH 2.0 with dilute hydrochloric acid and introduced into a chromatography column packed with 85 ml of activated charcoal ("Refined Shirasagi" brand for chromatography, manufactured by Takeda Chemical Co.) to adsorb leupeptins. The adsorbed leupeptins were eluted with 20% aqueous acetone. Active fractions of the eluate were combined and freed from acetone by distillation, giving an aqueous solution. This aqueous solution was neutralized to pH 5.5 with Dowex ® 44 (OH-form), and freeze-dried to yield 3.31 g of a pale yellow powder having a potency of 582 mcg/mg (total potency was 1,926 mg and the yield from the culture filtrate was 72%). The power was dissolved in 30 ml of methanol, introduced into a column packed with 90 g of acidic alumina together with methanol, and developed with methanol at a space velocity of 0.5. The active fractions of the effluent were combined and evaporated to dryness. The resulting powder was dissolved in water, filtered off the insolubles, and freeze-dried to obtain 1.85 g of L-leupeptin hydrochlorides having a potency of 988 mcg/mg. Total potency of the powder was 1,828 mg and the yield from the culture filtrate was about 69%. The L-form content of the powder was 100%.

EXAMPLE 2

Each 100 ml portion of a medium (pH 6.5) containing 2% glycerol, 1% polypeptone, and 1% meat extract was charged into 500 ml Erlenmeyer flasks, sterilized at 120° C for 30 minutes, inoculated with one platinum-loopful of a slant culture of *Streptomyces roseus*, MA839-

A1 (FERM-P No. 3,017, ATCC 31245), and shake-cultured at 27° C for 24 hours to yield a precultured broth. A 100 ml portion of another medium (pH 6.5) containing 3% glycerol, 0.75% L-leucine, 0.75% L-arginine hydrochloride, 0.75% glycine, 0.5% $NH_4NO_3$, 0.1% $K_2HPO_4$, 0.05% $MgSO_4.7H_2O$, 0.05% KCl, 0.2% ribonucleic acid, and 0.1% silicone defoamer was charged into a 500 ml flask, sterilized at 120° C for 30 minutes, then inoculated aseptically with 1 ml of the above precultured broth, and cultivated at 27° C for 3 days on a shake-culture machine operating at an amplitude of 7 cm and 210 reciprocations per minute. The progress of cultivation was as shown in Table 6.

Table 6

| Period of cultivation (hour) | Progress of culture | | |
|---|---|---|---|
| | 24 | 48 | 72 |
| pH | 6.7 | 5.9 | 5.7 |
| Leupeptin (mcg/ml) | 1,430 | 3,230 | 4,250 |

After 72 hours of cultivation, the cultured broth was filtered to remove the mycelium and the resulting filtrate (800 ml) having a leupeptin content of 4,070 mcg/ml was adjusted to pH 6 and passed through a column packed with 120 ml of Diaion HP 40 to adsorb leupeptin. After washing with water, the adsorbed leupeptin was eluted with 50% aqueous methanol of pH 2 to collect 235 ml of a leupeptin fraction. On removal of methanol by distillation at 40° C under reduced pressure from the leupeptin fraction, there was obtained 170 ml of an aqueous solution. This aqueous solution was adjusted to pH 5.5 with a dilute aqueous sodium hydroxide solution and extracted three times with 50 ml of n-butanol. The extract layers were combined and distilled at 40° C to remove the n-butanol as an azeotrope with water, and 100 ml of an aqueous solution containing 28 mg potency/ml of leupeptin was obtained. The aqueous solution thus obtained was adjusted to pH 2 with hydrochloric acid and the precipitate formed was removed by filtration. The filtrate was passed through a column packed with 100 ml of an activated charcoal ("Refined Shirasagi" brand, manufactured by Takeda Chemical Co.) to adsorb leupeptin. After washing with dilute hydrochloric acid of pH 2, the adsorbed leupeptin was eluted with 20% aqueous acetone of pH 2 to obtain 210 ml of a leupeptin fraction. The leupeptin fraction was adjusted to pH 5.0 with Dowex 44 resin (OH-form) and concentrated to dryness under reduced pressure to yield 4.00 g of a nearly white powder having an activity of 580 mcg/mg. The powder was dissolved in methanol, then passed through a column containing 60 g of an acidic alumina (manufactured by Woelm Co., F. R. Germany) suspended in methanol, and developed with methanol to collect leupeptin fractions. The combined leupeptin fraction was concentrated to dryness under reduced pressure to obtain 2.22 g of a white powder of leupeptin hydrochloride which showed a potency of 1,000 mcg/mg, the yield from the culture filtrate having been 68%.

The above powder had a specific rotatory power $[\alpha]_D^{23}$ of $-75°$ (c = 1, $H_2O$) and a melting point of 143° - 146° C (decomp.), showed positive Sakaguchi reaction, positive Rydon-Smith reaction, and negative ninhydrin reaction. It showed no specific absorption in ultraviolet region but an end absorption only. As shown in FIG. 2, the infrared absorption spectrum of the powder coincided with that of a DL-leupeptin obtained by a conventional process.

Twenty milligrams of the above hydrochlorides was hydrolyzed with 6 N hydrochloric acid in a sealed tube at 110° C for 24 hours and the free fatty acid in the hydrolyzate was extracted with ethyl ether. The extract layer was concentrated and subjected to gas chromatography using a column packed with Chromosolb 101 (60 - 80 mesh) (manufactured by Nippon Kuromato Kogyo Co.); only acetic acid was detected. Consequently, the powder was confirmed to be a leupeptin hydrochloride having only acetyl, as the acyl group.

Next, about 200 mg of the hydrochloride was dissolved in 8 ml of water. A solution of 52 mg of potassium permanganate in 2 ml of water was added dropwise to the above hydrochloride solution with stirring at room temperature and stirring was continued for further 2 hours to ensure oxidation. Thereafter, the excess potassium permanganate was neutralized with sodium thiosulfate and the resulting mixture was passed through a column packed with 5 ml of an activated charcoal. After washing with water, the adsorbed phase was eluted with 20% aqueous acetone of pH 2.0 to collect fractions which showed positive Sakaguchi reaction. These fractions were combined, adjusted to pH 5.0 with Dowex ® 44 resin (OH-form), and evaporated to dryness to yield 170 mg of a powder. The powder was dissolved in 1 ml of methanol and passed through a column filled with 5 g of an acidic alumina suspended in methanol and then developed with 15 ml of methanol followed by 25 ml of 50% aqueous methanol of pH 3.0. The effluent fractions giving positive Sakaguchi reaction were combined, adjusted to pH 5.0 with Dowex ® 44 resin (OH-form), and evaporated to dryness to give 75 mg of leupeptin acid (acyl-L-leucyl-L-leucyl-arginine). About 10 mg of this leupeptin acid was accurately weighed out, admixed with 2 ml of 6 N hydrochloric acid, and hydrolyzed in a sealed tube at 110° C for 24 hours. The hydrolyzate solution was evaporated to dryness and dissolved in water. A portion of the resulting solution was subjected to amino acid analysis to effect qualitative and quantitative analysis of the constitutive amino acids. The rest of the solution was subjected to bioassay using L-arginine-requiring lactic acid bacteria as the test organism to determine the L-arginine content. The results obtained were as shown in Table 7.

Table 7

| Amount of leupeptin acid used for hydrolysis | Composition of amino acids in the hydrolyzate of leupeptin acid | | |
|---|---|---|---|
| | Amino acid analysis | | |
| | L-leucine | Total arginine | L-arginine |
| 8.10 mg | 3.95 mg (30.1 μmol Recovery 89%) | 2.56 mg (14.8 μmol Recovery 87%) | 2.61 mg (102% of total argine) |

From the above results, it was concluded that the leupeptin acid which has undergone the hydrolysis had contained L-leucine and L-arginine in a molar ratio of 2 : 1 and none of the valine, isovaline, and D-arginine. Consequently, it was confirmed that the leupeptin obtained in the present Example is a single compound of acetyl-L-leucyl-L-leucyl-L-argininal.

EXAMPLE 3

One hundred milliliters of a medium (pH 6.5) containing 3% glycerol, 0.75% L-leucine, 0.75% L-arginine hydrochloride, 0.75% glycine, 0.5% $NH_4NO_3$, 0.1% $K_2HPO_4$, 0.05% $MgSO_4.7H_2O$, 0.5% KCl, and 0.1% silicone defoamer was charged into a 500 ml flask and sterilized at 120° C for 30 minutes. The sterilized medium was inoculated with 1 ml of a precultured broth prepared in the same manner as in Example 2, and cultivated at 27° C for 3 days on a reciprocating shake-culture machine operating at an amplitude of 7 cm and 210 machine operating at an amplitude of 7 cm and 210 reciprocations per minute. The progress of cultivation was as shown in Table 8.

Table 8

| Period of cultivation (hour) | Progress of cultivation | | |
|---|---|---|---|
| | 24 | 48 | 72 |
| pH | 6.6 | 6.3 | 5.9 |
| L-leupeptin (mcg/ml) | 830 | 1,610 | 2,460 |

From the culture filtrate (2,350 mcg/ml, 800 ml), L-leupeptin was extracted by the same way as in Example 2, except that Amberlite XAD-4 was used in place of Diaion HP40, and 1.22 g of L-leupeptin hydrochloride was obtained.

EXAMPLE 4

One hundred milliliters of a midium (pH 6.5) containing 3% glucose, 0.75% L-leucine, 0.75% L-arginine hydrochloride, 0.75% glycine, 0.8% $(NH_4)_2SO_4$, 0.1% $K_2HPO_4$, 0.05% $MgSO_4.7H_2O$, 0.05% KCl, 0.2% ribonucleic acid, and 0.1% silicone defoamer was charged into a 500 ml flask and sterilized at 120° C for 30 minutes. The sterilized medium was inoculated with 1 ml of a seed culture broth prepared in the same manner as in Example 2, and cultivated at 27° C for 3 days on a reciprocating shake-culture machine operating at an amplitude of 7 cm and 210 reciprocations per minute. The progress of culture was as shown in Table 9.

Table 9

| Period of cultivation (hour) | Progress of culture | | |
|---|---|---|---|
| | 24 | 48 | 72 |
| pH | — | 4.8 | 7.0 |
| L-leupeptin (mcg/ml) | — | 3,170 | 4,050 |

From the culture filtrate (3,880 mcg/ml, 800 ml), L-leupeptin was extracted and purified by the same way as in Example 2, except that Diaion HP20 was used instead of Diaion HP40, and 1.96 g of L-leupeptin hydrochloride was obtained.

EXAMPLE 5

Each 100 ml portion of a medium (pH 6.5) containing 3% glycerol, 2% peptone, 0.5% L-leucine, 0.5% L-arginine hydrochloride, 0.5% glycine, 0.5% NaCl, 0.2% $KH_2PO_4$, 0.1% ribonucleic acid, and 0.05% silicone defoamer was charged into 500 ml flasks and sterilized at 120° C for 20 minutes. Each portion was then inoculated with 1 ml of a precultured broth prepared in the same manner as in Example 2, and cultivated at 27° C for 3 days on a shake-culture machine operating at an amplutide of 7 cm and 210 reciprocations per minute. The results obtained were as shown in Table 10.

Table 10

| Period of cultivation (hour) | Progress of culture | | |
|---|---|---|---|
| | 24 | 48 | 72 |
| pH | 6.5 | 6.3 | 6.6 |
| L-leupeptin (mcg/ml) | 1,060 | 2,580 | 3,870 |

From the culture filtrate (3,700 mcg/ml, 800 ml), L-leupeptine was isolated by the same way as in Example 2, except that Diaion HP30 was used instead of Diaion HP40, and 1.93 of L-leupeptin hydrochloride was obtained.

EXAMPLE 6

Twenty liters of a medium (pH 6.5) containing 3% glycerol, 0.75% L-leucine, 0.75% L-arginine hydrochloride, 0.75% glycine, 0.5% $NH_4NO_3$, 0.1% $K_2HPO_4$, 0.05% $MgSO_4.7H_2O$, 0.05% KCl, 0.2% ribonucleic acid, and 0.05% silicone defoamer was charged into a 30-liter jar fermentor and sterilized at 120° C for 30 minutes. The sterilized medium was inoculated with 200 ml of a seed culture broth prepared in the same manner as in Example 2 and cultured at 27° C for 48 hours under the following conditions; speed of agitator, 400 r.p.m.; air-flow rate, 20 liters per minute. The progress of culture was as shown in Table 11.

Table 11

| Period of cultivation (hour) | Progress of culture | | | |
|---|---|---|---|---|
| | 24 | 36 | 42 | 48 |
| pH | 6.5 | 5.0 | 5.3 | 5.5 |
| L-leupeptin (mcg/ml) | 1,550 | 3,400 | 4,250 | 4,450 |

From the culture filtrate (4,350 mcg/ml, 800 ml each), L-leupeptin was isolated by the same way as in the Example 2, except that Amberlite XAD-1, XAD-5, XAD-7, XAD-8, Diaion HP10, HP50 and Duolite S-30 were used instead of Diaion HP40, and 2.05 g, 2,20 g, 1.80 g, 1.75 g. 2.18 g, 2.22 g and 2.01 g of L-leupeptin hydrochloride were obtained, respectively.

What is claimed is:

1. A process for producing L-leupeptins, which comprises inoculating a leupeptins-producing strain of Streptomyces into one member selected from the group consising of (A) medium containing each 0.5 to 1.25% (wt/vol) of L-leucine, L-arginine (as hydrochloride), and glycine and (B) medium containing each 0.5 to 1.25% (wt/vol) of L-leucine, L-arginine (as hydrochloride), and glycine and 0.05 to 0.3% (wt/vol) of at least one member selected from the group consisting of yeast extract, casein hydrolyzate, and ribonucleic acids, cultivating aerobically said strain under the condition of pH 5.0 to 7.0 to produce and accumulate L-leupeptins in the medium, and extracting and purifying the L-leupeptins from the culture broth under the condition of pH 7.0 or less.

2. A process according to claim 1, wherein the medium does not contain more than 0.3% (wt/vol) of any amino acids or any substances containing amino acids other than L-leucine, L-arginine and glycine to form acetyl-L-leucyl-L-leucyl-L-argininal.

3. A process according to claim 1, wherein the extraction and purification is carried out by use of a porous nonionic adsorbent resin.

4. A process according to claim 3, wherein the porous nonionic adsorbent resin is a member selected from the group consisting of styrene-divinyl-benzene copolymer, acrylic ester polymer, and phenolic resin.

5. A process according to claim 3, wherein the porous nonionic adsorbent resin is Amberlite XAD-1, Amberlite XAD-2, Amberlite XAD-4, Amberlite XAD-5, Diaion HP10, Diaion HP20, Diaion HP30, Diaion HP40 or Diaion HP50.

6. A process according to claim 1, wherein the leupeptins-producing strain is *Streptomyces roseus* MA839-A1 (FERM-P No. 3019, ATCC 31245).

7. A process according to claim 1, wherein the leupeptins-producing strain is *Streptomyces roseus* MB262-M1, *Streptomyces roseochloromogenes* MA943-M1, *Streptomyces roseochromogenes* MB456-AE1, *Streptomyces roseochromogenes* MB260-A2, *Streptomyces chartreusis* MB58-MB1, *Streptomyces albireticuli* MB26-A1, *Streptomyces thioluteus* MB321-A1, *Streptomyces lavendulae* MB172-A2, or *Streptomyces noboritoensis* MB46-AG.

* * * * *